United States Patent [19]

Schroeder et al.

[11] Patent Number: 4,808,751

[45] Date of Patent: Feb. 28, 1989

[54] METHOD FOR REACTIVATING A GROUP VIII NOBLE METAL CATALYST FOR USE IN THE PURIFICATION OF CRUDE TEREPHTHALIC ACID

[75] Inventors: Hobe Schroeder, Warrenville; Ricky L. Wittman, Montgomery, both of Ill.

[73] Assignee: Amoco Corporation, Chicago, Ill.

[21] Appl. No.: 174,850

[22] Filed: Mar. 29, 1988

[51] Int. Cl.$^4$ .................... C07C 51/42; C07C 63/26; B01J 23/96; B01J 20/20
[52] U.S. Cl. ...................... 562/487; 502/25; 502/26
[58] Field of Search ............ 502/25, 26; 562/486, 562/487

[56] References Cited

U.S. PATENT DOCUMENTS

| | | | |
|---|---|---|---|
| 4,263,452 | 4/1981 | Komatsu et al. | 562/486 |
| 4,629,715 | 12/1986 | Schroeder | 502/185 |
| 4,728,630 | 3/1988 | Schroeder et al. | 502/185 |

FOREIGN PATENT DOCUMENTS

| | | | |
|---|---|---|---|
| 0036436 | 4/1975 | Japan | 562/487 |
| 1085929 | 10/1967 | United Kingdom | 562/487 |

*Primary Examiner*—Paul E. Konopka
*Attorney, Agent, or Firm*—James R. Henes; William H. Magidson; Ralph C. Medhurst

[57] ABSTRACT

A method is disclosed for reactivating a Group VIII noble metal catalyst employed in the purification of crude terephthalic acid formed by the liquid-phase oxidation of p-xylene in the presence of a catalyst comprising cobalt, manganese and bromine components.

19 Claims, No Drawings

METHOD FOR REACTIVATING A GROUP VIII NOBLE METAL CATALYST FOR USE IN THE PURIFICATION OF CRUDE TEREPHTHALIC ACID

BACKGROUND OF THE INVENTION

1. Field of the Invention

This invention relates generally to a method for reactivating a catalyst comprising a Group VIII noble metal and more particularly concerns a method for reactivating the aforesaid catalyst for use in the purification by hydrogenation of crude terephthalic acid produced by the liquid phase oxidation of p-xylene in the presence of a catalyst comprising cobalt, manganese and bromine components.

2. Discussion of the Prior Art

Polymer grade or "purified" terephthalic acid is the starting material for polyethylene terephthalate, which is the principal polymer for polyester fibers, polyester films, and resins for bottles and the like containers. Purified terephthalic acid is derived from relatively less pure, technical grade or "crude" terephthalic acid by purification of the latter utilizing hydrogen and a noble metal catalyst as described in Meyer, U.S. Pat. No. 3,584,039.

Impurities present in crude terephthalic acid include partially-oxidized products such as p-toluic acid and 4-carboxybenzaldehyde. These impurities are usually present in the crude terephthalic acid in relatively significant amounts. In addition, color-forming precursors and color bodies that are believed to be of the benzil, fluorenone and/or anthraquinone type are present as impurities. While p-toluic acid is an impurity that can be readily removed from crude terephthalic acid solutions by wellknown cooling-and-crystallization techniques, other impurities such as 4-carboxybenzaldehyde and the aforesaid color forming precusors and color bodies are more difficult to remove from crude terephthalic acid solutions.

One approach to purification of crude terephthalic acid involves first converting the 4-carboxybenzaldehyde to a more soluble product that is more readily separable upon crystallization of the terephthalic acid. To that end, aqueous solutions of crude terephthalic acid are hydrogenated in the presence of a noble-metal catalyst, such as palladium on an active carbon support. This hydrogenation step also converts the various color forming precusors and color bodies present in the crude terephtahlic acid to colorless products. Another related purification-by-hydrogenation process for aromatic polycarboxylic acid produced by the liquid phase catalytic oxidation of polyalkyl aromatic hydrocarbons is described in Stech et al., U.S. Pat. No. 4,405,809. Other such purification-by-hydrogenation processes have suggested using a combination noble metal catalyst e.g., a palladium/rhodium (Pd/Rh) catalyst on a porous carbonaceous support for purification of crude aqueous terephthalic acid solutions. (See, e.g., Puskas et al., U.S. Pat. Nos. 4,394,299 and 4,467,110.)

However, for reasons that have not generally been fully understood, a marked decrease with time has been observed in the activity of the aforesaid noble metal catalyst employed in the aforesaid purification step. The occurrence of this catalytic deactivation is highly undesirable from the standpoint of large commercial operations. In particular, such decrease in catalyst activity is disadvantageous in continuous or semi-continuous operations wherein the catalyst is used for relatively long periods of time. Eventually such catalysts must be taken out of service and replaced by fresh catalysts as product specifications for purified terephthalic acid are exceeded. Therefore, it is essential to develop a method for reactivating the aforesaid noble metal catalyst for use in the aforesaid purification by hydrogenation of crude terephthalic acid.

Methods have been disclosed for reactivating a catalyst comprising a Group VIII metal by washing the catalyst with an alkaline solution. For example, Miller, U.S. Pat. No. 3,650,983, discloses that a palladium catalyst which is employed in the synthesis of vinyl acetate from ethylene, acetic acid and oxygen experiences a serious decrease in catalytic activity during the aforesaid synthesis of vinyl acetate and that the activity of this catalyst for the same synthesis can be regenerated by washing the catalyst with an alkaline solution. Miller discloses furthermore that neither the amount of the alkaline solution employed per given weight of the catalyst nor the concentration of alkali metal or alkaline earth metal salt or hydroxide in the alkaline solution is critical, and each can vary over a wide range. For example, the concentration of the alkali metal or alkaline earth metal salt or hydroxide in the alkaline solution can be 0.25 to 30 percent by weight, and the amount of alkaline solution employed can be 0.1 to 10 liters per 350 grams of catalyst. The regeneration is carried out at ambient temperature and pressure.

Yamauchi et al., U.S. Pat. Nos. 4,147,660; 4,190,554 (a continuation-in-part of U.S. Pat. No. 4,147,660) and 4,228,033 (a divisional of U.S. Pat. No. 4,190,554) disclose that a platinum group catalyst which is employed in the catalytic reaction of hydrocarbons (optionally containing an oxygen atom) suffers a loss of catalytic activity during the course of the catalytic reaction and that the activity of such catalyst for the same reaction can be regenerated by contact with at least one agent selected from an inorganic alkaline substance and a reducing substance in an aqueous medium. The inorganic alkaline substance may be an inorganic alkaline compound containing at least one alkali metal or alkaline earth metal. The concentration of the inorganic alkaline substance in the aqueous medium may be varied depending upon the amount of the catalyst component deposited on the carrier material, the degree of lowered catalytic activity, the temperature and pressure at which the reactivation treatment is carried out and the like. In general, however, the concentration of the inorganic alkalene substance in the aqueous medium is usually from about 0.001 to 10N, preferably from about 0.001 to 5N. The temperature at which the treatment with the inorganic alkaline substance is performed is generally from about 5° C. to 250° C. and can be varied widely depending on the extent of lowered catalytic activity, the composition of the catalyst, and the kind of the inorganic alkaline substance employed. The pressure is typically selected so as to maintain the aqueous system for the aforesaid treatment in a liquid state.

It is also known in the art to employ a multi-step wash of the aforesaid noble metal catalyst first with hot water at 250° C.–300° C., second with cooler water at 20° C.–100° C. and third with a dilute solution of from about 4 to about 8 weight percent of sodium hydroxide in order to reactivate the aforesaid catalyst for use in the purification by hydrogenation of crude terephthalic acid. However, those of ordinary skill in the art to which this invention pertains have avoided the use of more concentrated solutions of alkali or alkaline earth metals on the belief that such solutions would be deleterious to the efficacy of the noble metal catalyst in the purification by hydrogenation of crude terephthalic acid. Furthermore, there is no known prior use or disclosure of a sequence of wash steps involving a wash with a more concentrated solution of from about 12 to about 30 weight percent of ammonium or alkali or alkaline earth metal ions.

It has now been found that the stability of commercially available noble metal-on-carbon catalysts in the aforesaid purification by hydrogenation of crude terephthalic acid (produced by the liquid phase oxidation of p-xylene in the presence of a catalyst comprising colbalt, manganese and bromine components) can be improved and their useful catalytic lifetimes in such purification extended by the practice of the method of the present invention.

OBJECTS OF THE INVENTION

It is therefore a general object of the present invention to provide an improved method for reactivating a catalyst comprising a Group VIII metal to avoid the aforementioned loss in catalytic activity for the aforesaid purification of crude terephthalic acid produced by the aforesaid liquid-phase oxidation of p-xylene in the presence of a catalyst comprising cobalt, manganese and bromine components.

A related object of the present invention is to provide an improved process for the production of purified terephthalic acid by the purification of crude terephthalic acid produced by the aforesaid liquid-phase oxidation of p-xylene.

These and other objects and advantages of the invention will become apparent upon reading the following detailed description and appended claims.

SUMMARY OF THE INVENTION

These objects are achieved by the method of this invention for use in combination with a method for producing purified terephthalic acid comprising: oxidizing p-xylene in the liquid phase with an oxygen-containing gas in a solvent at an elevated temperature and pressure and in the presence of an oxidation catalyst comprising cobalt, manganese, and bromine components to form crude terephthalic acid and impurities comprising 4-carboxybenzaldehyde, color bodies and color-forming precursors; reducing in the liquid phase in a purification reactor at least a portion of the aforesaid impurities in the resulting crude terephthalic acid in an aqueous solution at an elevated temperature and pressure and in the presence of hydrogen and at least one insoluble Group VIII noble metal-containing catalyst; withdrawing the aqueous solution from the purification reactor; and crystallizing and separating the solid noble metal-containing catalyst from the aqueous solution. The method of this invention for reactivating the purification catalyst comprises: (a) after the aqueous solution of terephthalic acid is withdrawn from the purification reactor, contacting the purification catalyst with hot water at a temperature in the range of from about 200° C. to about 350° C. for from about 0.5 to about 10 hours; (b) contacting the purification catalyst with cool water at a temperature in the range of from about 3° C. to about 100° C. for from about 0.5 to about 10 hours; and (c) contacting the purification catalyst with a concentrated alkaline solution of from about 12 to about 30 weight percent of a hydroxide or salt ammonium or an alkali or alkaline earth metal for from about 1 to about 10 hours.

DETAILED DESCRIPTION OF THE PREFERRED EMBODIMENTS

Suitable solvents for use in the oxidation step of the method for producing purified terephthalic acid for use in combination with the method of this invention include any aliphatic $C_2$-$C_6$ monocarboxylic acid such as acetic acid, propionic acid, n-butyric acid, isobutyric acid, n-valeric acid, trimethylacetic acid, and caproic acid, and water, and mixtures thereof. Preferably, the solvent is a mixture of acetic acid and water, which more preferably contains from 1 to 20 weight percent of water, as introduced into the oxidation reactor (that is, exclusive of water produced in the oxidation reaction). Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude terephthalic acid product from the product stream, at least a portion of the mother liquor (solvent) in the resulting product stream is generally recycled to the reactor.

The source of molecular oxygen employed in the oxidation step of the method for producing purified terephthalic acid for use in combination with the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method for producing purified terephthalic acid for use in combination with the method of this invention comprises cobalt, manganese, and bromine components, and can additionally comprise accelerators known in the art. The weight ratio of cobalt (calculated as elemental cobalt) in the cobalt component of the catalyst-to-p-xylene in the liquid-phase oxidation is in the range of from about 0.2 to about 10 milligram atoms (mga) per gram mole of p-xylene. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquidphase oxidation is in the range of from about 0.1 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable bromine sources include elemental bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzyl-bromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

In operation, the minimum pressure at which the oxidation reactor is maintained is that pressure which will maintain a substantial liquid phase of the p-xylene and at least 70 percent of the solvent. The p-xylene and solvent not in the liquid phase because of vaporization are removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 $kg/cm^2$ to about 35 $kg/cm^2$, and typically are in the range of from about 10 $kg/cm^2$ to about 30 $kg/cm^2$. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

Crude terephthalic acid produced by the liquid-phase oxidation of p-xylene is generally purified by reduction of the impurities therein, for example, by the methods disclosed in the aforesaid U.S. Pat. Nos. 3,584,039; 3,726,915; and 4,405,809. The purification step of the method for producing purified terephthalic acid for use in combination with the method of the present invention is conducted at an elevated temperature and pressure in the presence of a fixed catalyst bed. The crude terephthalic acid to be purified is dissolved in water or a like polar solvent. Although water is the preferred solvent, other suitable polar solvents include the relatively lower molecular weight alkyl carboxylic acids, alone or admixed with water. Suitable reactor temperatures for use in this purification step are in the range of from about 100° C. to about 350° C. Preferably, the temperatures employed in the purification step are in the range of about 275° C. to about 300° C.

The pressure employed in the purification step depends primarily upon the temperature employed therein. Inasmuch as the temperatures at which practical amounts of the impure terephthalic acid may be dissolved in an aforesaid solvent are substantially above the normal boiling point of the solvent, the process pressures are necessarily considerably above atmospheric pressure to maintain the solution in liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 200 to about 1,500 pounds per square inch gauge (psig), and usually is in the range of about 900 psig to about 1,200 psig.

The reactor employed in the purification step can be operated in several modes. For example, a predetermined liquid level can be maintained in the reactor, and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative amounts of hydrogen and inert gas present in the admixture.

In yet another operating mode, the reactor can be filled with the terephthalic acid solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution.

In general, the amount of hydrogen supplied to the purification reactor under reaction conditions is, of course, sufficient to effect the desired hydrogenation.

As described in the aforesaid U.S. Pat. Nos. 3,584,039; 3,726,915; and 4,405,809, catalysts that are suitable for use in the aforesaid purification step are insoluble under the conditions employed therein and comprise at least one supported or unsupported Group VIII noble metal, which class includes palladium, rhodium, ruthenium, osmium, iridium, and platinum. Preferably, the noble metal is at least one of palladium and rhodium.

Preferably, the catalyst comprises an inert support. Preferred support materials include carbon and charcoal. Typically, the catalyst carrier is active carbon, usually that derived from coconut charcoal in the form of granules having a surface area of at least about 600 $m^2/g$ ($N_2$; BET Method), preferably about 800 $m^2/g$ to about 1,500 $m^2/g$. However, other porous carbonaceous supports or substrates can be used as long as the surface area requirements can be met. In addition to coconut charcoal, activated carbon derived from other plant or from animal sources can be utilized.

The noble metal component is present on the carrier at a concentration level in the range of about 0.01 weight percent to about 2 weight percent, based on the total weight of the catalyst, i.e., metal plus active carbon carrier, and calculated as the elemental noble metal Preferably, the catalyst metal loading is about 0.5 weight percent.

A typical catalyst of palladium on a support comprises from about 0.01 to about 2 weight percent of palladium, based on the total weight of the catalyst and calculated as elemental metal. The support or carrier for the palladium is porous and inert, and preferably is active carbon having a surface area of about 600 $m^2/g$ about 1,500 $m^2/g$. Suitable supports for Pd/C hydrogenation catalysts are well-known and are described, inter alia, in Meyer, U.S. Pat. No. 3,584,039.

A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Engelhard Corporation, under the designations "Rhodium on Activated Carbon Granules, (Carbon Code CG-5)." and "Rhodium on Activated Carbon Grandules (Carbon Code CG-21)." Both of these catalysts have a BET $N_2$ surface area of about 1,000 $m^2/g$ and have a particle size of $4 \times 8$ mesh, U.S. Sieve Series. Other suitable rhodium-on-carbon catalysts of similar size and surface area are available from Johnson Matthey Inc., Seabrook, New Hampshire under the designation "11766 Rhodium, 1% on Steam Activated Carbon Grandules, Anhydrous."

The space velocity reported as weight of crude terephthalic acid solution per weight of catalyst per hour in the purification step is from about 5 hours$^{-1}$ to about 25 hours$^{-1}$, preferably from about 10 hours$^{-1}$ to about 15 hours$^{-1}$. The residence time of the solution in the catalyst bed varies, depending upon the activity of the catalysts present.

We have discovered that, in the method of the present invention, a very effective method for reactivating the aforesaid purification catalyst comprises a multi-step washing process. In a first step, after the aqueous solution of purified terephthalic acid is withdrawn from the purification reactor, the purification catalyst is contacted with hot water at a temperature in the range of from about 200° C., preferably from about 250° C., to about 350° C., preferably to about 300° C., for from about 0.5, preferably from about 1, to about 10, preferably to about 5 hours.

In a second step, the purification catalyst is contacted with relatively cooler water at a temperature in the range of from about 3° C., preferably from about 20° C., to about 100° C., preferably to about 50° C., for from about 0.5, preferably from about 1, to about 10, preferably to about 5 hours.

In a third step, the purification catalyst is contacted with a relatively concentrated alkaline solution of from about 12, preferably from about 16, to about 30, preferably to about 24 weight percent, of an alkaline substance for from about 1, preferably from about 2, to about 10, preferably to about 5 hours. Such contacting in this fourth step is performed at a temperature preferably from about 3° C., more preferably from about 20° C., preferably to about 100° C., more preferably to about 50° C.

Preferably, in the method of the present invention, after contacting the catalyst with the aforesaid cooler water and before contacting the purification catalyst with the relatively concentrated alkaline solution, the purification catalyst is contacted with a relatively dilute alkaline solution of from about 2, preferably from about 4, to about 10, preferably to about 8 weight percent of an alkaline substance for from about 0.5, preferably from about 1, to about 10, preferably to about 5 hours. Such contacting in this step is performed at a temperature preferably from about 3° C., more preferably from about 20° C., preferably to about 100° C., more preferably to about 50° C.

The alkaline substances employed in the aforesaid relatively dilute and relatively concentrated alkaline solutions can be the same or different and are each soluble in the specific solvent employed for each such contacting solution under the conditions employed in the respective step, and contain at least one alkali metal or alkaline earth metal or ammonium organic acid salt, or inorganic acid salt, hydroxide, or a mixture thereof. The alkali metal and alkaline earth metal salts of weak acids, both organic carboxylic acids having from 2 to 18 carbon atoms and inorganic acids, have been found especially useful as the alkaline components. A useful salt or hydroxide is one whose aqueous solution has a pH greater than about 7. The salts may have anions such as citrate, acetate, borate, phosphate, tartrate, benzoate, aluminate, and the like. Examples of the alkali metals and alkaline earth metals are sodium, potassium, calcium, magnesium, barium, strontium, etc. Preferred examples of the inorganic alkaline compounds containing ammonium or these alkali metals and alkaline earth metals are the hydroxides, carbonates, nitrates, sulfates, etc., or mixtures thereof.

Preferably, each alkaline solution employed in the reactivation procedure of the method of this invention is an aqueous solution. However, solvents other than and in addition to water may be employed and include such conventional solvents as alkanols, nitriles, esters, etc. Specific examples of such other solvents are methanol, ethanol, isopropanol, acetonitrile, dioxane, and the like. Mixtures of solvents may also be utilized. The reactivation procedure of the present invention will hereinafter be illustrated with respect to the use of an aqueous alkaline solution.

The minimum pressure at which each step in the reactivation procedure of the method of this invention is performed is that pressure which will maintain the various solvents and solutions employed in the method of this invention in the liquid phase. In general, the minimum pressure required to meet this requirement depends on the specific temperature employed in the respective step.

The purification catalyst can be contacted with the liquid employed in each respective step of the reactivation procedure of the method of this invention by any convenient method. Typically either of two procedures is used. First, the reactor can be filled with the respective liquid at least to the level necessary to cover the purification catalyst particles in it. The catalyst particles are then left to soak, and then the liquid is drained from the catalyst particles. Second, the other procedure involves continuously or intermittently passing the respective liquid through the catalyst particles in the purification reactor. Preferably, in the first and second steps of the method of this invention, the water is passed downwardly through the catalyst bed from a point in the upper portion of the purification reactor; and the alkaline solution(s) employed in the remaining step(s) are passed upwardly through the catalyst bed from a point in the lower portion of the purification reactor.

The present invention will be more clearly understood from the following examples.

EXAMPLES 1-8

Examples 1-8 involve a number of runs in each of which p-xylene is oxidized in the liquid phase to crude terephthalic acid in a continuous stirred tank reactor having titanium-lined inside walls and then the purification by hydrogenation of the resulting crude terephthalic acid in a reactor containing a fixed bed of purification catalyst through which an aqueous solution of the crude terephthalic acid is passed continuously. In the continuous oxidations of Examples 1-8, oxidation reactor effluent slurries comprising crude terephthalic acid were produced from a feed comprising the catalyst, acetic acid, 2 weight percent of water and a fixed concentration of p-xylene. The oxidations were performed at a constant temperature in the range of 150° C. to 230° C. and a constant absolute pressure in the range of 10 kg/cm$^2$ to 30 kg/cm$^2$. The oxidation reactor was equipped with an overhead condenser for condensation of the solvent and p-xylene which vaporized in the reactor during the exothermic liquid phase oxidation and also for return of the condensed material to the reaction mixture in the reactor. The solvent introduced into the oxidation reactor from the overhead condenser was a mixture of acetic acid and water which contained 14-15 weight percent of water. The catalyst comprised cobalt, manganese and bromine components which were in the form of soluble $Co(C_2H_3O_2.4H_2O)$, $Mn(C_2H_3O_2)_2.4H_2O$ and hydrobromic acid, respectively. The ratio of the number of gram atoms of the manganese component, calculated as elemental manganese, per gram atom of the cobalt component, calculated as elemental cobalt, was in the range of 1:1 to 6:1, and the ratio of the number of gram atoms of the bromine component, calculated as elemental bromine, per gram atom of the combined cobalt and manganese components, calculated as elemental cobalt and elemental manganese was 0.15:1 to 1:1. The residence times in the oxidations of Examples 1-8 were between 60 and 90 minutes. In each oxidation, the oxygen concentration (measured on a solvent-free basis) in the gas-vapor mixture in the condenser was between 0.5 and 5 mole percent.

In each of Examples 1-8, the liquid effluent from the oxidation reactor, comprising an aqueous solution containing about 30 weight percent of crude terephthalic acid, was fed continuously to a fixed bed reactor containing a relatively fresh Pd-on-carbon catalyst (about 0.5 wt-% Pd). Gaseous hydrogen was dissolved in the solution under pressure just prior to the time the solution entered the catalyst bed and the hydrogen partial pressure within the reactor was monitored. The optical density of the aqueous feed solution to the reactor was also measured using light at 340 nm wavelength ($OD_{340}$).

The resulting hydrogenated terephthalic acid solution was cooled sufficiently to precipitate the purified terephthalic acid present, the resulting precipitate was then separated from the liquid phase present, washed with water, and dried.

In each of Examples 1-8, flow of the aqueous solution of crude terephthalic acid into the purification reactor was interrupted and after the aqueous solution of purified terephthalic acid was withdrawn from the purification reactor, water at 280° C. was passed downwardly through the purification reactor and catalyst bed from a point substantially at the top of the reactor at a rate of about 15 pounds of water per pound of catalyst per hour for 2 hours. Thereafter, water at 30° C. was passed downwardly through the purification reactor from a point substantially at the top of the purification reactor at a rate of about 15 pounds of water per pound of catalyst per hour for 2 hours. Then the purification reactor was filled by a solution of 5 weight percent of sodium hydroxide in water at 20° C. that had been passed upwardly from a point substantially at the bottom thereof, and the catalyst was soaked in this alkaline solution (about 1.5 pounds of water per pound of catalyst per hour) for at least one hour.

Next the purification catalyst was treated by either of two different approaches. In Examples 1-4, the purification catalyst was washed by deionized, distilled water at 20° C. passing downwardly through the purification reactor from a point substantially at the top thereof at a rate of 15 pounds of water eer pound of catalyst per hour for 2 hours. By contrast, in Examples 5-8, a solution of 20 weight percent of sodium hydroxide in water at 20° C. was passed upwardly through the purification reactor from a point substantially at the bottom thereof at a rate of about 1.5 pounds of solution per pound of catalyst per hour for 3 hours. Finally, deionized distilled water was passed through the purification reactor as described above in respect to Examples 1-4. In respect of all of the other experimental conditions employed, the same conditions were employed in each of Examples 1-8.

In each of Examples 1-8, the 4-carboxybenzaldehyde content and b*-value were measured (1) for the crude terephthalic acid prior to purification, (which were in each example about 3000 parts per million by weight of 4-carboxybenzaldehyde and a b*-value of about 4), and for the purified terephthalic acid produced therefrom (2) immediately before the purification catalyst was reactivated and (3) one day and (4) two days after the purification catalyst was reactivated. The results of these measurements are shown in Tables 1 and 2.

The results shown in Tables 1 and 2 demonstrate that the use of the higher concentration alkaline solution in the method of this invention regenerates the purification catalyst to a greater extent for longer periods of time than does the use of only the lower concentration alkaline solution. Relative to its activity level immediately prior to being regenerated, purification catalyst that has been regenerated by the use of the more concentrated alkaline solution demonstrates improved catalytic activity even after purification catalyst that has been regenerated by the use of the less concentrated alkaline solution no longer demonstrates the benefits of regeneration.

TABLE 1

| Reactivation With | 4-Carboxybenzaldehyde Content (ppm by Wt.) of Purified Terephthalic Acid | | |
|---|---|---|---|
| | Before React. | After Reactivation 1 Day | 2 Days |
| 5% NaOH | | | |
| Example 1 | 18.5 | 9.2 | 16.6 |
| Example 2 | 15.0 | 10.0 | 16.2 |
| Example 3 | 16.4 | 12.7 | 23.0 |
| Example 4 | 16.0 | 16.6 | 16.5 |
| Mean | 16.5 | 12.1 | 18.1 |
| 20% NaOH | | | |
| Example 5 | 30.0 | 8.7 | 11.1 |
| Example 6 | 16.3 | 10.8 | 13.0 |
| Example 7 | 19.5 | 14.5 | 17.8 |
| Example 8 | 19.4 | 17.4 | 18.3 |
| Mean | 21.3 | 12.9 | 15.0 |

TABLE 2

| Reactivation With | b*-Value of Purified Terephthalic Acid | | |
|---|---|---|---|
| | Before React. | After Reactivation 1 Day | 2 Days |
| 5% NaOH | | | |
| Example 2 | 0.68 | 0.46 | 0.50 |
| Example 3 | 0.78 | 0.76 | 0.79 |
| Example 4 | 0.58 | 0.72 | 0.76 |
| Mean | 0.68 | 0.65 | 0.68 |
| 20% NaOH | | | |
| Example 5 | 0.61 | 0.47 | 0.57 |
| Example 6 | 0.65 | 0.45 | 0.57 |
| Example 7 | 0.69 | 0.62 | 0.68 |
| Example 8 | 0.68 | 0.58 | 0.68 |
| Mean | 0.66 | 0.53 | 0.63 |

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. In combination with a method for producing purified terephthalic acid comprising: oxidizing p-xylene in the liquid-phase with an oxygen-containing gas in a solvent at an elevated temperature and pressure and in the presence of an oxidation catalyst comprising cobalt, manganese, and bromine components to form crude terephthalic acid and impurities comprising 4-carboxybenzaldehyde, color bodies and color-forming precursors; reducing in the liquid phase in a purification reactor at least a portion of the aforesaid impurities in the resulting crude terephthalic acid in solution at an elevated temperature and pressure and in the presence of hydrogen and a bed of a particulate purification catalyst comprising at least one insoluble Group VIII noble metal; withdrawing the solution from the purification reactor; and crystallizing and separating the purified terephthalic acid from the solution;

a method for reactivating the purification catalyst, comprising:
 (a) after the solution of purified terephthalic acid is withdrawn from the purification reactor, contacting the purification catalyst with hot water at a temperature in the range of from about 200° C. to about 350° C. for from about 0.5 to about 10 hours;
 (b) contacting the purification catalyst with cool water at a temperature in the range of from about 3° C. to about 100° C. for from about 0.5 to about 10 hours; and
 (c) contacting the purification catalyst with a concentrated alkaline solution of from about 12 to about 30 weight percent of a salt or hydroxide of ammonium or an alkali or alkaline earth metal for from about 1 to about 10 hours.

2. The method of claim 1 wherein, after step (b) is performed and before step (c) is performed, the purification catalyst is contacted a dilute alkaline solution of from about 2 to about 10 weight percent of a salt or hydroxide of ammonium or an alkali or alkaline earth metal for from about 1 to about 10 hours.

3. The method of claim 2 wherein the dilute alkaline solution employed is at a temperature in the range of from about 3° C. to about 100° C.

4. The method of claim 2 wherein the dilute alkaline solution employed contains from about 4 to about 8 weight percent of the hydroxide or salt.

5. The method of claim 2 wherein the dilute alkaline solution employed contains a hydroxide of sodium, potassium or ammonium.

6. The method of claim 2 wherein the purification catalyst is contacted with the dilute alkaline solution employed for from about 1 to about 5 hours.

7. The method of claim 2 wherein the solvent of the dilute alkaline solution employed is water.

8. The method of claim 1 wherein the alkaline solution employed in step (c) is at a temperature in the range of from about 3° C. to about 100° C.

9. The method of claim 1 wherein the concentrated alkaline solution employed contains from about 16 to about 24 weight percent of the hydroxide or salt.

10. The method of claim 1 wherein the concentrated alkaline solution employed contains a hydroxide of ammonium, sodium or potassium.

11. The method of claim 1 wherein the purification catalyst is contacted with the concentrated alkaline solution for from about 1 to about 5 hours.

12. The method of claim 1 wherein the solvent in the concentrated alkaline solution employed in step (c) is water.

13. The method of claim 1 wherein after step (c), the purification catalyst is washed with distilled or deionized water.

14. The method of claim 1 wherein the solvent in the oxidation step is a $C_2$–$C_6$ monocarboxylic acid, water or a mixture thereof.

15. The method of claim 14 wherein the solvent in the oxidation step is a mixture of acetic acid and water containing from 1 to 20 weight percent of water in the reactor.

16. A method of claim 1 wherein the catalyst in the purification step comprises at least one Group VIII noble metal-containing component on a carbon support.

17. The method of claim 16 wherein the catalyst in the purification step comprises at least a palladium-containing component on a carbon support.

18. The method of claim 1 wherein the oxidation step is performed at a temperature in the range of from about 120° C. to about 240° C.

19. The method of claim 1 wherein the purification step is performed at a temperature in the range of from about 100° C. to about 350° C.

* * * * *